United States Patent
Tanaka

(10) Patent No.: US 8,545,397 B2
(45) Date of Patent: Oct. 1, 2013

(54) ENDOSCOPE SHAPE ANALYSIS APPARATUS

(75) Inventor: Hideki Tanaka, Tama (JP)

(73) Assignee: Olympus Medical Systems Corp., Tokyo (JP)

( * ) Notice: Subject to any disclaimer, the term of this patent is extended or adjusted under 35 U.S.C. 154(b) by 728 days.

(21) Appl. No.: 12/752,325

(22) Filed: Apr. 1, 2010

(65) Prior Publication Data
US 2010/0191056 A1    Jul. 29, 2010

Related U.S. Application Data

(63) Continuation of application No. PCT/JP2008/062936, filed on Jul. 17, 2008.

(30) Foreign Application Priority Data

Oct. 2, 2007  (JP) .................................. 2007-259120
Oct. 11, 2007  (JP) .................................. 2007-265679

(51) Int. Cl.
*A61B 1/00*        (2006.01)

(52) U.S. Cl.
USPC ............................................ 600/117; 600/145

(58) Field of Classification Search
USPC .................. 600/117, 118, 145, 150, 422–424
See application file for complete search history.

(56) References Cited

U.S. PATENT DOCUMENTS

| | | | |
|---|---|---|---|
| 6,511,417 B1 | 1/2003 | Taniguchi et al. | |
| 8,251,890 B2 * | 8/2012 | Tanaka | 600/103 |
| 2005/0228221 A1 | 10/2005 | Hirakawa | |

FOREIGN PATENT DOCUMENTS

| | | |
|---|---|---|
| EP | 1 504 712 A1 | 2/2005 |
| JP | 04-146716 | 5/1992 |
| JP | 2000-175861 | 6/2000 |
| JP | 2003-245242 | 9/2003 |
| JP | 2004-358095 | 12/2004 |

* cited by examiner

*Primary Examiner* — Clayton E Laballe
*Assistant Examiner* — Minh Phan
(74) *Attorney, Agent, or Firm* — Scully, Scott, Murphy & Presser, P.C.

(57) ABSTRACT

An endoscope shape analysis apparatus includes a coordinates obtaining portion for obtaining coordinate values of an insertion portion; a storage portion for storing the coordinate values; a straight line setting portion for setting a first straight line A and a second straight line B, based on the coordinate values; a coordinate transformation portion for transforming coordinates of a previous second straight line B1, based on a positional relationship between a previous first straight line A1 and the first straight line A, to calculate a third straight line B2; a determination portion for determining whether there is an error in a position display from a positional relationship between the first straight line A, the second straight line B, and the third straight line B2; and a correction portion for correcting the second straight line B.

19 Claims, 16 Drawing Sheets

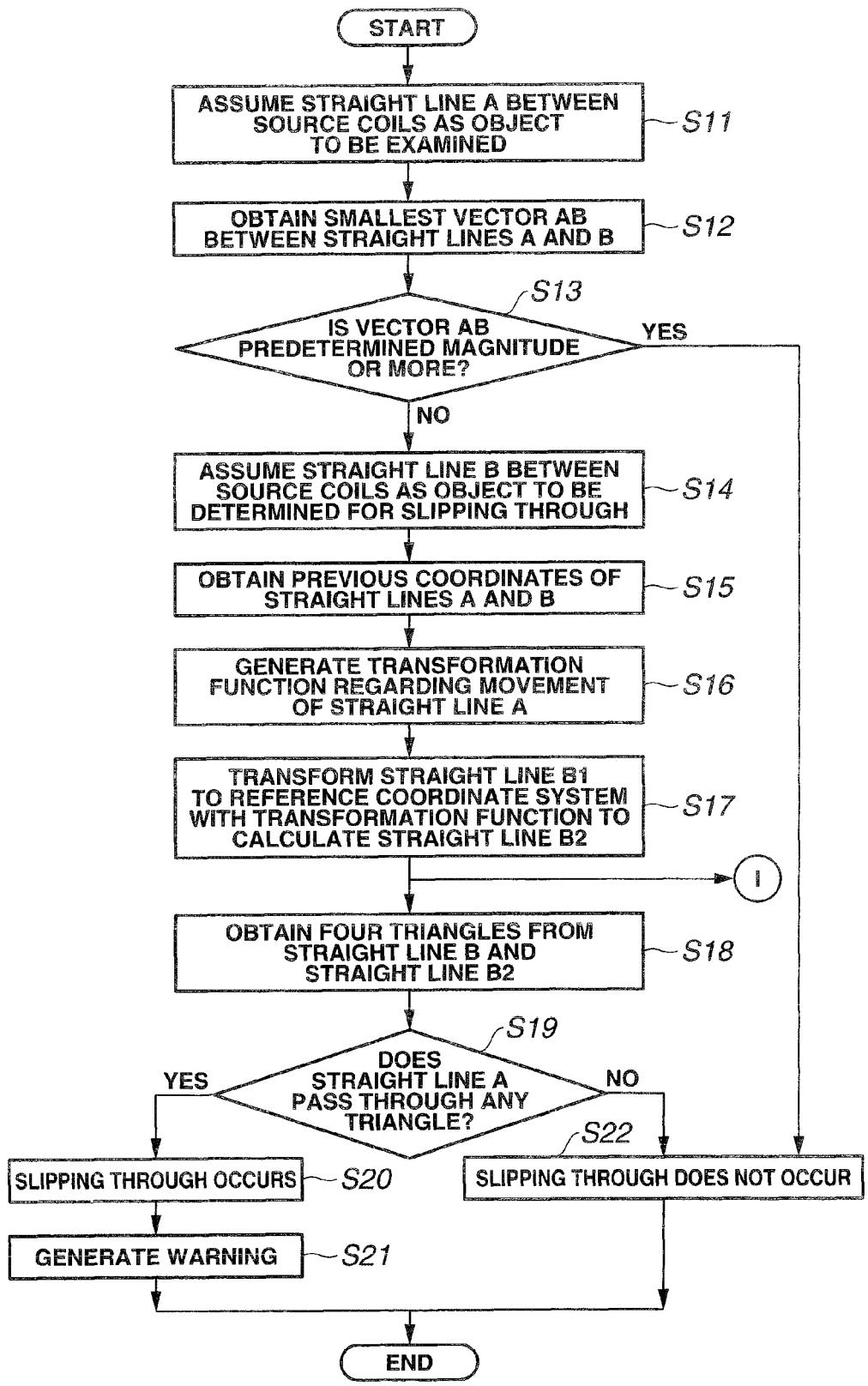

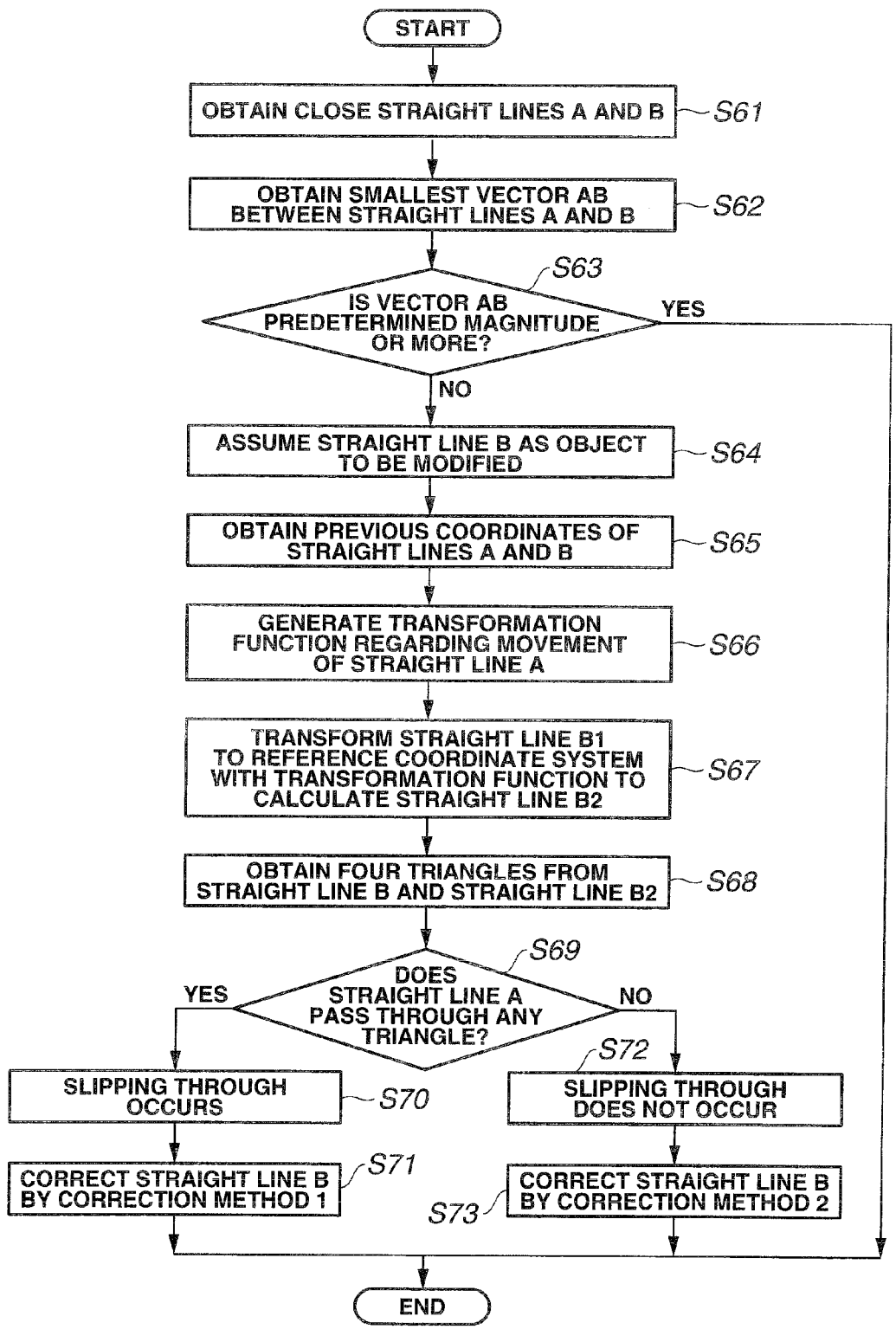

US 8,545,397 B2

ENDOSCOPE SHAPE ANALYSIS APPARATUS

CROSS REFERENCE TO RELATED APPLICATION

This application is a continuation application of PCT/JP2008/062936 filed on Jul. 17, 2008 and claims benefit of Japanese Applications No. 2007-259120 filed in Japan on Oct. 2, 2007, and No. 2007-265679 filed in Japan on Oct. 11, 2007, the entire contents of which are incorporated herein by their reference.

BACKGROUND OF INVENTION

1. Field of the Invention

The present invention relates to an endoscope shape analysis apparatus, and particularly to an endoscope shape analysis apparatus having a coordinates obtaining portion for detecting coordinate values in a plurality of places.

2. Description of the Related Art

An endoscope is adapted to externally insert an elongated insertion portion having flexibility into a test portion, which is a lumen in a body cavity, to observe the test portion and perform necessary treatment. But, the lumen in the body cavity is bent as observed in a large intestine and a small intestine, and an operator can not easily see to what position the inserted insertion portion is inserted, or in what shape the inserted insertion portion is. Therefore, conventionally, a test body portion into which the insertion portion is inserted is externally irradiated with X-rays to detect an insertion state, such as a position and shape of insertion of the insertion portion into a lumen. But, the X-rays are not harmless to a human body. Besides, an irradiation place is limited, and therefore, the X-rays are not always preferred as a method for detecting the insertion state of the insertion portion.

Accordingly, an apparatus and method for detecting an insertion state of an endoscope or a catheter are proposed in which by disposing a plurality of magnetic field generating devices in an insertion portion and using a magnetic field sensing portion outside a body cavity, without having a physiological adverse effect on a human body, a state of insertion of the insertion portion into a lumen in the body cavity can be detected. Further, when the insertion portion is inserted into a large intestine and the like, the insertion portion may form a spiral loop in a free portion where the intestine is not fixed to an abdominal cavity and the like. Insertion operation in such a state in which the insertion portion forms a loop, that is, a state in which the intestine is deformed in a loop shape, causes pain to a patient. Therefore, Japanese Patent Application Laid-Open Publication No. 2000-175861 discloses an endoscope shape detection apparatus that can recognize occurrence of a loop of an insertion portion during insertion and generate a warning to an operator.

Also, Japanese Patent Application Laid-Open Publication No. 2003-245242 discloses a method in which since a number of magnetic field generating devices disposed in an insertion portion to measure a shape of the insertion portion is limited, a position of the insertion portion between magnetic field generating devices is made up for by an interpolation process.

The endoscope shape detection apparatus disclosed in Japanese Patent Application Laid-Open Publication No. 2000-175861 detects a shape of an insertion portion by a combination of a plurality of magnetic field generating devices disposed in the insertion portion, and a magnetic field sensing portion outside a body cavity.

As shown in FIG. 1A, the endoscope shape detection apparatus can obtain three-dimensional coordinates of, for example, eight magnetic field generating devices C1 to C8, by a combination of the plurality of magnetic field generating devices disposed in the insertion portion, and a magnetic field sensing portion outside a body cavity. The endoscope shape detection apparatus can sense a shape of the insertion portion by interpolating for coordinate points, as shown in FIG. 1B.

Position information of a winding direction of the loop is very important for an operator because a rotation direction of the insertion portion operated by the operator to eliminate the loop is different depending on the way in which the loop is wound, as shown in FIG. 2.

FIG. 2A shows a loop in which a distal end portion 20a side of the insertion portion 20 is closer to the operator than a proximal end portion 20b side. To eliminate the loop shown in FIG. 2A, the operator needs to rotate the proximal end portion 20b side of the insertion portion clockwise. On the other hand, in a loop shown in FIG. 2B, the distal end portion 20a side of the insertion portion 20 is on a further side from the operator than the proximal end portion 20b side. To eliminate the loop shown in FIG. 2B, the operator needs to rotate the proximal end portion 20b side of the insertion portion counterclockwise.

A position display error phenomenon in which a way in which a loop of an insertion portion is wound is erroneously reversely displayed is called "slipping through" because, for example, a change from a state in which the insertion portion on a distal end side is at a position closer to an operator than the insertion portion on a proximal end side (FIG. 2A) to a state in which the insertion portion on the distal end side is at a position farther from to the operator than the insertion portion on the proximal end side (FIG. 2B) is seen as if the insertion portion on the distal end side slips through the insertion portion on the proximal end side.

Further, even if a shape display of the insertion portion 20 is correctly displayed without an error, as shown in FIG. 2C, distinction as to which of the insertion portion on the distal end portion 20a side and the insertion portion on the proximal end portion 20b side is at a position closer to the operator may be difficult in an intersection portion of the loop. The discrimination difficulty phenomenon in the intersection portion of the loop is a phenomenon caused by a three-dimensional endoscope shape being displayed on a two-dimensional display screen.

SUMMARY OF THE INVENTION

An endoscope shape analysis apparatus of the present invention includes a coordinates obtaining portion for obtaining a plurality of coordinate values of an insertion portion; a storage portion for storing the obtained plurality of coordinate values; a straight line setting portion for setting a first straight line and a second straight line, a position of which is compared with a position of the first straight line, based on the plurality of coordinate values; a coordinate transformation portion for transforming coordinates of a previous second straight line, based on a relative positional relationship between a previous first straight line stored in the storage portion and a current first straight line, to calculate a third straight line; and a determination portion for determining whether there is an error in a position display of the insertion portion from a positional relationship between the current first straight line, the current second straight line, and the third straight line.

Also, an endoscope shape analysis apparatus of the present invention includes a coordinates obtaining portion for obtaining a plurality of coordinate values of an insertion portion; a storage portion for storing the obtained plurality of coordinate values; a straight line setting portion for setting a first straight line and a second straight line having a shortest vector of smallest magnitude from the first straight line, based on the plurality of coordinate values; a coordinate transformation portion for transforming coordinates of a previous second straight line, based on a relative positional relationship between a previous first straight line stored in the storage portion and a current first straight line, to calculate a third straight line; a determination portion for determining whether there is the error in a position display of the insertion portion from a positional relationship between the current first straight line, the current second straight line, and the third straight line; and a correction portion for correcting the second straight line, based on determination of the determination portion.

BRIEF DESCRIPTION OF THE DRAWINGS

FIG. 4 is a flow chart for explaining a flow of operation of the endoscope shape analysis apparatus in the first embodiment;

FIG. 12 is a flow chart for explaining a flow of operation of the endoscope shape analysis apparatus in the third embodiment;

DETAILED DESCRIPTION OF THE PREFERRED EMBODIMENT(S)

Embodiments of the present invention will be described below with reference to the drawings.

First Embodiment

Figure 1A:
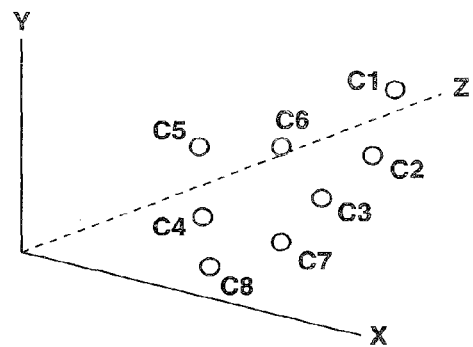
FIGS. 1A and 1B are diagrams for explaining detection of an endoscope shape by an endoscope shape detection apparatus.
Figure 1B:
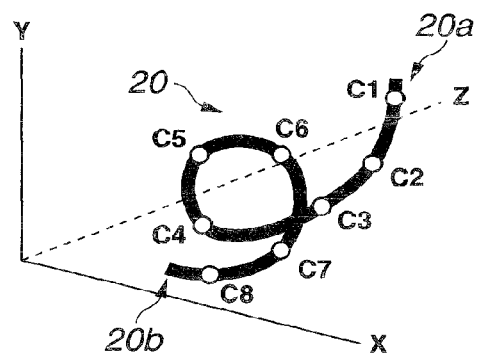
Figure 2A:
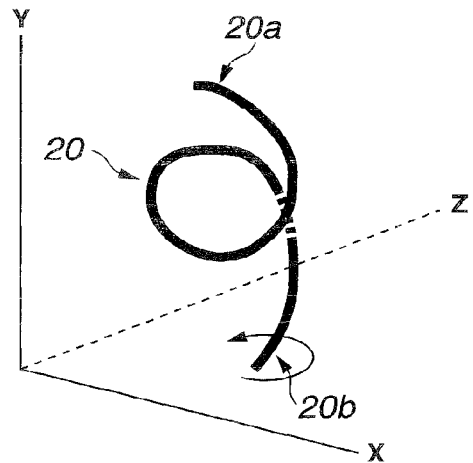
FIGS. 2A and 2B are diagrams for explaining a way in which a loop of an insertion portion is wound, and a method for eliminating the loop.
Figure 2B:
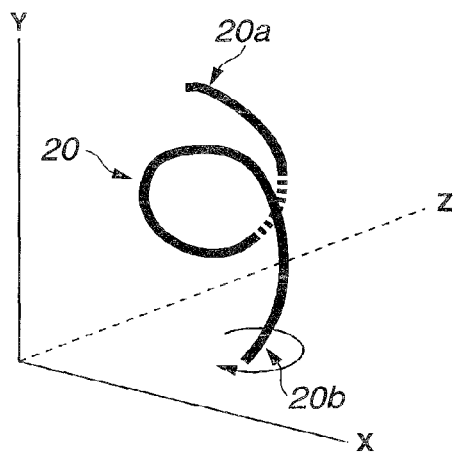
Figure 2C:
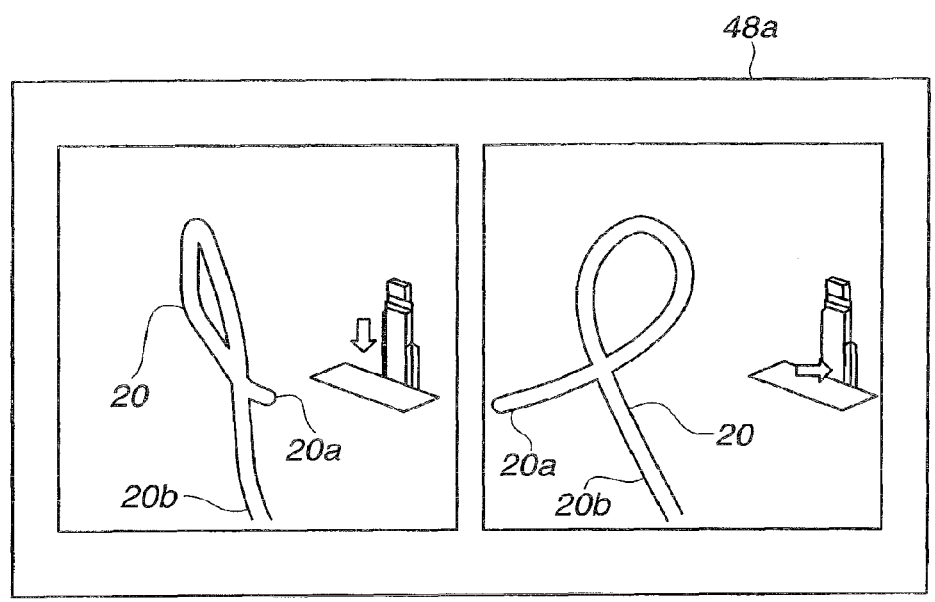
FIG. 2C is a diagram showing an example of display of a loop intersection portion of the insertion portion.
Figure 3:
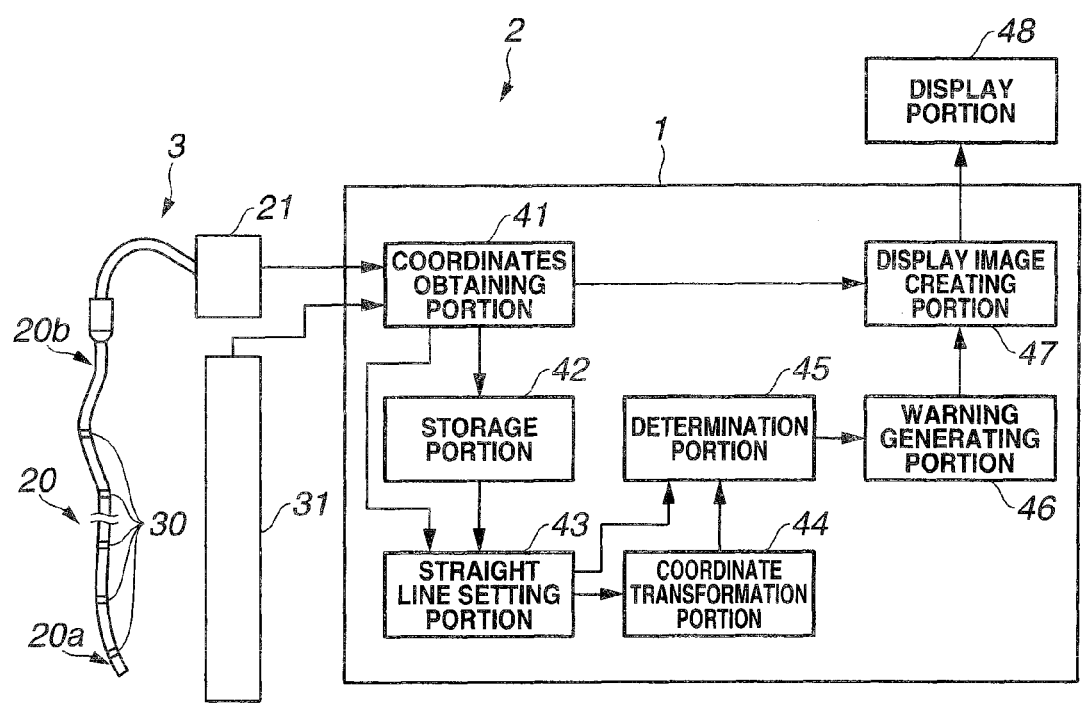
FIG. 3 is a configuration diagram for explaining a configuration of an endoscope shape analysis apparatus in a first embodiment.

As shown in FIG. 3, an endoscope system 2 in the present embodiment includes an endoscope apparatus 3 for performing endoscopy, and the endoscope shape analysis apparatus 1 connected to the endoscope apparatus 3 and used for assistance of endoscopy. The endoscope shape analysis apparatus 1 is used as an insertion assisting portion, for example, when an elongated insertion portion 20 having flexibility is inserted into a body cavity of a patient (not shown) lying on a bed to perform endoscopy. The endoscope system 2 has usual endoscope functions, such as a light source portion, an image pickup device, and a control portion, each not shown.

The insertion portion 20 is constituted by sequentially connecting a distal end portion 20a, a bending portion, and a flexible tube from the distal end portion 20a to a proximal end portion 20b. A forceps channel is provided in the insertion portion 20, and by inserting, for example, a probe having a plurality of source coils 30 as magnetism generating devices, into an insertion opening of the forceps channel, the source coils 30 are placed in the insertion portion 20. Alternatively, an endoscope having the insertion portion 20 in which the source coils 30 are previously disposed may be used.

Wiring extended from a back end of the source coil probe, and connected to the source coils 30, is connected to the endoscope shape analysis apparatus 1 via a terminal 21. By applying high frequency signals (driving signals) from a coordinates obtaining portion 41 of the endoscope shape analysis apparatus 1, the source coils 30 emit magnetic fields around.

Also, a sensing coil unit 31 containing a plurality of sensing coils for detecting magnetic fields from the source coils 30 is located near the bed (not shown) on which the patient lies.

A detailed configuration of the endoscope shape analysis apparatus 1 will be described below. The endoscope shape analysis apparatus 1 has a coordinates obtaining portion 41 for driving the source coils 30 and obtaining coordinate values of the source coils 30 from signals received by the sensing coil unit 31, a storage portion 42, which is a storage portion for storing the obtained plurality of coordinate values, a straight line setting portion 43 for setting a first straight line A and a second straight line B, a position of which is compared with a position of the first straight line, based on the coordinate values of the plurality of source coils 30, a coordinate transformation portion 44 for transforming coordinates of a previous second straight line B1, based on a relative positional relationship between a previous first straight line A1 stored in the storage portion and a current first straight line A, to calculate a third straight line B2, and a determination portion 45 for determining whether there is an error in position display of the insertion portion 20 from a positional relationship between the current first straight line A, the current second straight line B, and the third straight line B2.

Also, the endoscope shape analysis apparatus 1 has a display image creating portion 47 for displaying an endoscope shape from the coordinate values of the source coils 30, a display portion 48 for displaying the endoscope shape, and a warning generating portion 46 for generating a warning, based on information from the determination portion 45.

The plurality of source coils 30, that is, magnetic field generating coils, are disposed in the insertion portion 20 in specific positions at predetermined intervals. Intervals at which the source coils 30 are disposed need not be equal. For example, the source coils 30 may be more densely disposed on a distal end side than on a proximal end side.

By driving the respective source coils 30 by driving signal currents having sine waves at different frequencies, three-dimensional coordinates of the respective source coils 30 are distinguished and obtained. A method for obtaining spatial position coordinates, that is, three-dimensional coordinates, of the source coils 30 by the coordinates obtaining portion 41 is disclosed in Japanese Patent Application Laid-Open Publication No. 2000-175861 and the like filed earlier by the present applicant, and the three-dimensional coordinates of the source coils 30 are also obtained by a similar method in the present embodiment. Therefore, detailed description is omitted.

Next, a method for determining whether there is an error in position display of the insertion portion 20, that is, whether a "slipping through" phenomenon occurs, by the endoscope shape analysis apparatus 1 in the present embodiment will be described using FIG. 4 to FIG. 7C.

The method for determining whether there is an error in position display of the insertion portion 20, that is, whether a "slipping through" phenomenon occurs, by the endoscope shape analysis apparatus 1 will be described below according to the flow chart of FIG. 4.

<Step S11 and Step S12>

Figure 5A:
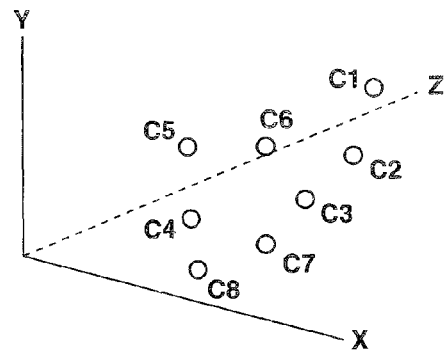
FIGS. 5A to 5D are explanatory diagrams for explaining operation of a straight line setting portion in the first embodiment.

In the following description, for simplicity of explanation, shape analysis of an endoscope having the insertion portion 20 in which eight source coils C1 to C8 are disposed in specific places, as shown in FIG. 5A, will be described.

First, the straight line setting portion 43 sets a first straight line A and a second straight line B to be examined as to whether a position display error occurs, that is, to be determined as to whether a "slipping through" phenomenon occurs, based on a plurality of coordinate values from the coordinates obtaining portion 41.

Figure 5B:
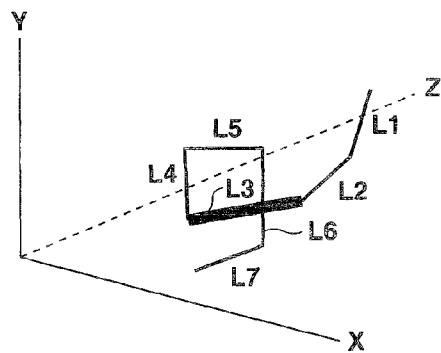
Figure 5C:
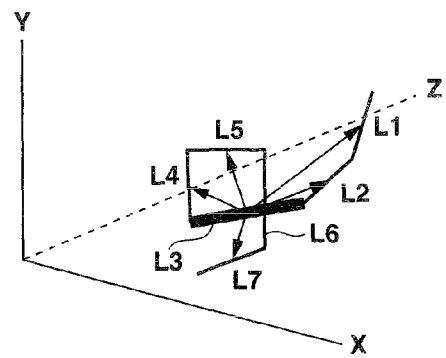
Figure 5D:
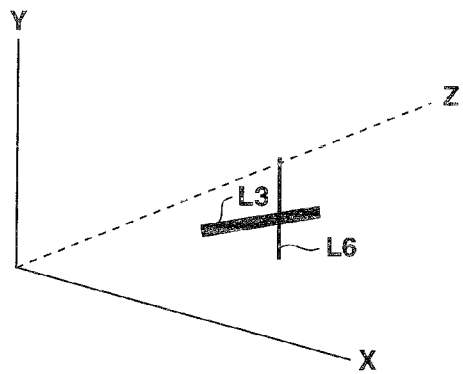

The straight line setting portion 43 calculates seven straight lines L1 to L7 connecting neighboring source coils, as shown in FIG. 5B. For example, the straight line setting portion 43 calculates vectors from a barycenter (midpoint) of selected one straight line L3 to barycenters (midpoints) to other straight lines, as shown in FIG. 5C. Further, the straight line setting portion 43 calculates vectors to barycenters (midpoints) to other straight lines, in order, for all the seven straight lines, except for vectors different only in direction from the vectors that have already been calculated. The straight line setting portion 43 sets the straight lines L3 and L6, which have base points of a vector of smallest magnitude (shortest vector) among a total of 21 vectors, as the first straight line A and the second straight line B respectively.

Even when the straight line L3 is the second straight line B, and L6 is the first straight line A, the following processes are similar, and a similar result is obtained. Also, the straight line setting portion 43 need not calculate vectors between all straight lines and may calculate only straight lines that were relatively close to each other at the time of last straight line setting.

For a shortest vector AB, instead of using a barycenter (midpoint) of each straight line as a reference, a vector AB of smallest magnitude between the straight line A and the straight line B may be used as a reference.

<Step S13>

When a magnitude of the shortest vector AB calculated in step S12 is a predetermined value or more (Yes), a "slipping through" phenomenon does not occur, and therefore, the endoscope shape analysis apparatus 1 determines that "slipping through does not occur" (step S22).

In other words, a "slipping through" phenomenon occurs when a magnitude F of the above-described shortest vector is in a relationship shown by the following expression, wherein d is a diameter of the endoscope, and t is a thickness of a test body wall (intestinal wall).

$$F < K = k \times (d+2t)$$

Here, k is 5 or less, preferably 3 or less, though K depends on content of treatment and an extent of a position information detection error of the endoscope shape analysis apparatus 1, When the above range is exceeded, a "slipping through" phenomenon does not occur because a distance between neighboring insertion portions 20 exceeds the position information detection error.

<Step S14>

When the magnitude F of the shortest vector AB calculated in step S12 is less than the predetermined value K: $k \times (d+2t)$ (No), the endoscope shape analysis apparatus 1 performs processes in step S15 and subsequent steps, assuming the straight line B as an object to be determined in which a "slipping through" phenomenon can occur.

<Step S15>

The coordinate transformation portion 44 obtains from the storage portion 42 previous coordinate values of the source coils at both ends of two straight lines (the first straight line and the second straight line) set by the straight line setting portion.

The storage portion 42 stores coordinate values of the source coils in a time series manner. Here, storing in a time series manner means storing previous coordinate values of the source coils together with time information. A cycle in which the coordinate values of the source coils are obtained is, for example, about 0.01 to 1 second, and the storage portion 42 stores at least coordinate values of the source coils obtained by the coordinates obtaining portion 41 last time. When the previous coordinate values of the source coils stored by the storage portion 42 are only the coordinate values of the source coils obtained last time, it is unnecessary to store time information.

The previous coordinate values obtained by the coordinate transformation portion 44 are coordinate values obtained by the coordinates obtaining portion 41 last time, or coordinate values obtained by the coordinates obtaining portion 41 for a predetermined period previously designated by an operator, for example, 1 to 5 seconds before, because optimum previous coordinate values are different depending on a speed of insertion of the endoscope by the operator.

<Step S16>

The coordinate transformation portion 44 generates a transformation function regarding movement of the first straight line A.

Figure 6A:
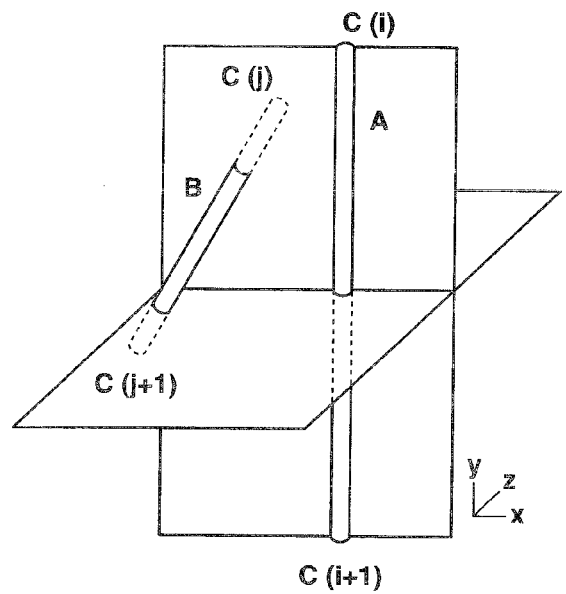
FIGS. 6A to 6E are explanatory diagrams for explaining operation of a coordinate transformation portion in the first embodiment.
Figure 6B:
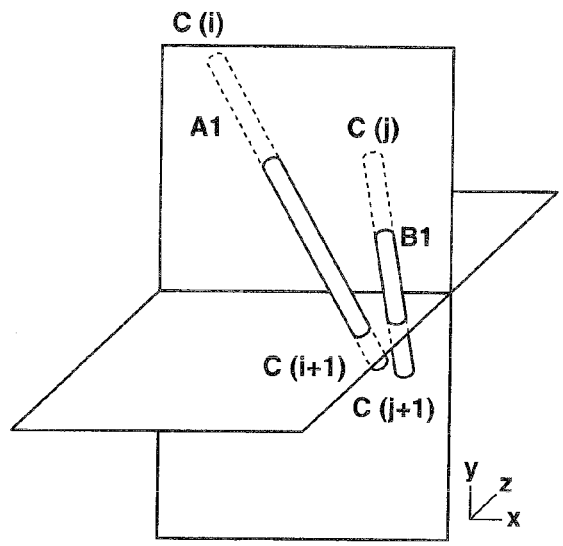

A case where with respect to a first straight line A and a second straight line B in a current state shown in FIG. 6A, a previous first straight line A1 and a previous second straight line B1 are in a state shown in FIG. 6B will be described below as an example. The first straight lines A and A1 are straight lines connecting coordinate values detected by source coils C(i) and C(i+1) respectively, and the second straight lines B and B1 are straight lines connecting coordinate values detected by source coils C(j) and C(j+1) respectively.

Figure 6C:
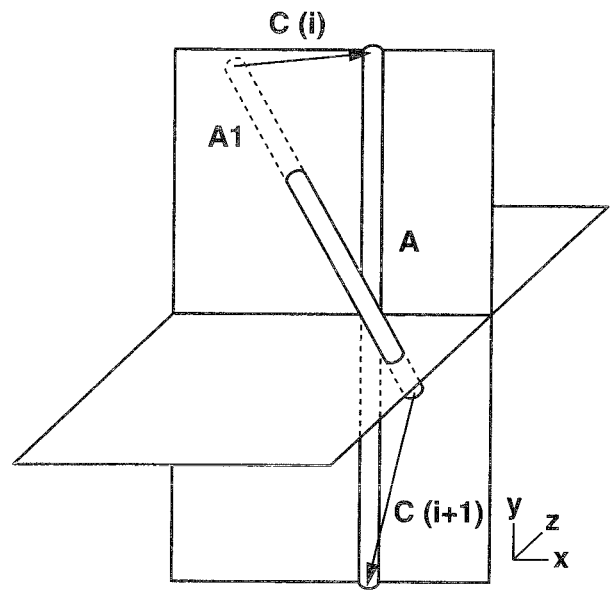

In other words, for the first straight lines A and A1, the source coils C(i) and C(i+1) move as shown in FIG. 6C. Movement is translation and rotation movement of a barycenter (center) of a vector C(i) C(i+1) connecting the source coils C(i) and C(i+1) and can be represented by a transformation function.

As a transformation function used for transformation, for example, a quaternion can be used. A quaternion is a quaternary, and a quaternion showing a relationship between two vectors p and q is generated by the following procedure. First, an outer product r of the vector p and the vector q is obtained.

Here, the outer product r is orthogonal to the vector p and the vector q. Next, an angle θ formed by the vector p and the vector q is obtained by an inner product. Then, a quaternion that rotates by θ around the outer product r as an axis is generated.
<Step S17>

Figure 6D:
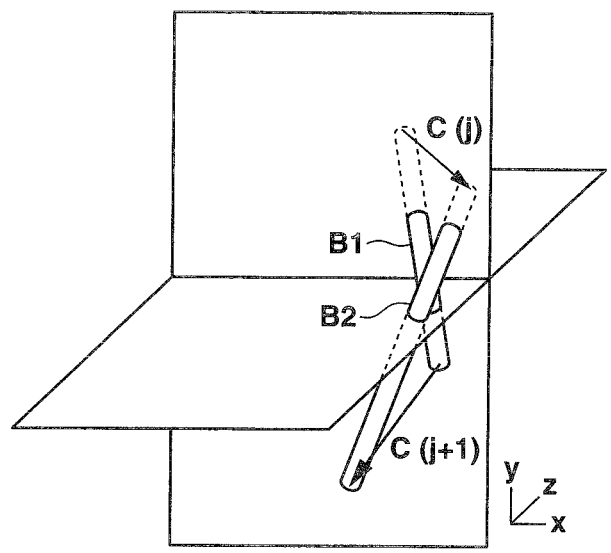

The coordinate transformation portion 44 transforms the previous second straight line B1 to a reference coordinate system based on the current first straight line A, with the transformation function regarding movement of the first straight line A generated in step S16, to calculate a third straight line B2, as shown in FIG. 6D. In other words, the coordinate transformation portion 44 transforms coordinates of the previous second straight line B1, based on a relative positional relationship between the previous first straight line A1 stored in the storage portion 42 and the current first straight line A, to calculate the third straight line B2. The third straight line B2 shows a position of the previous second straight line B1 in a state in which the first straight line A does not move at all.

Figure 6E:
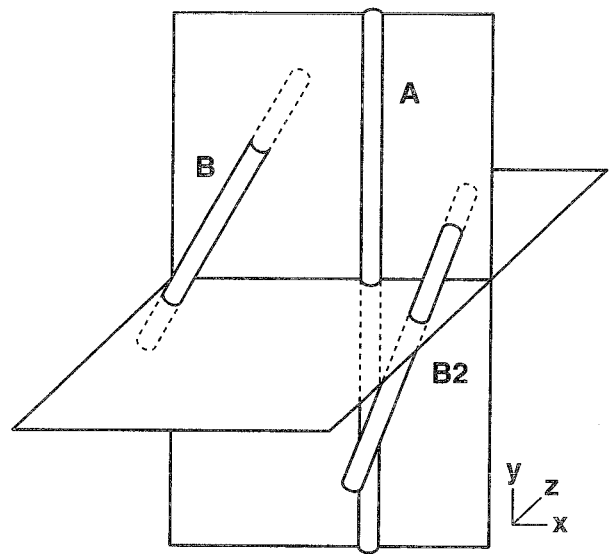

In other words, it is seen that with respect to the first straight line A, the second straight line B moves from a position of the third straight line B2 to a current position, as shown in FIG. 6E.

The determination portion 45 determines whether a "slipping through" phenomenon occurs from positions of the first straight line A, the second straight line B, and the third straight line B2 shown in FIG. 6E.

Indication (I) in FIG. 4 is a branch to a process of the endoscope shape analysis apparatus 1B in a second embodiment.
<Step S18>

Figure 7A:
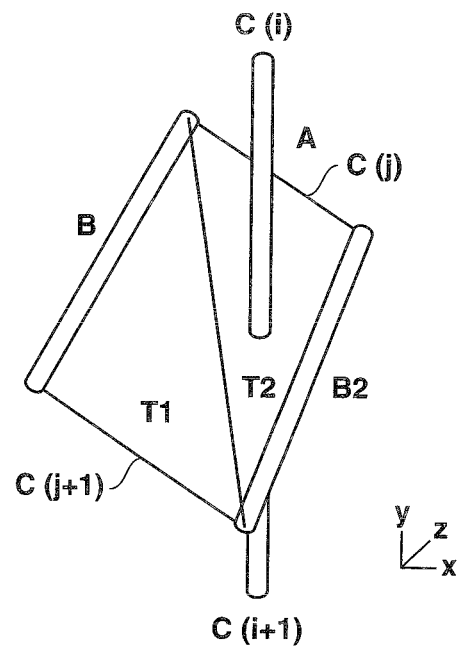
FIGS. 7A to 7C are explanatory diagrams for explaining operation of a determination portion in the first embodiment.
Figure 7B:
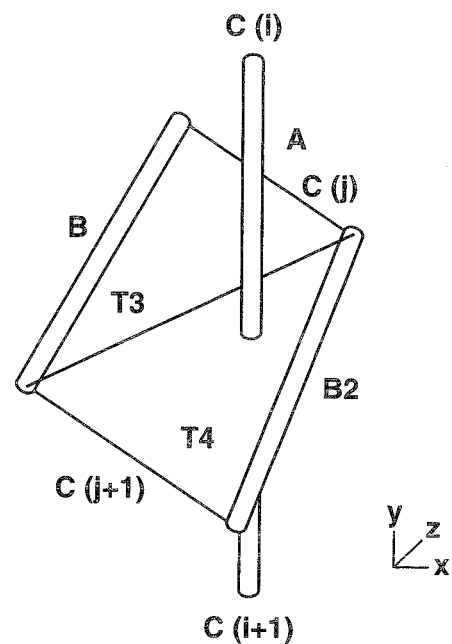

The determination portion 45 of the endoscope shape analysis apparatus 1 in the present embodiment obtains triangles having any three points, among four points of both ends of the current second straight line B and both ends of the third straight line B2, as vertexes, as shown in FIG. 7A and FIG. 7B. Here, there are four triangles having any three points, among four points of both ends of the second straight line B and both ends of the third straight line B2, as vertexes, as shown by T1 to T4 in FIG. 7A and FIG. 7B.
<Step S19>

The determination portion 45 of the endoscope shape analysis apparatus 1 in the present embodiment determines that there is an error in position display of the insertion portion 20 when the current first straight line A passes through any of four triangles having any three points, among four points of the both ends of the current second straight line B and the both ends of the third straight line B2, as vertexes, as shown in FIG. 7A and FIG. 7B, (Yes) (step S20). On the contrary, the determination portion 45 determines that there is no error in position display of the insertion portion 20 when the current first straight line A does not pass through any of the four triangles (No) (step S22).

In other words, the determination portion 45 determines that a "slipping through" phenomenon occurs when the first straight line A passes through a plane of one or more of the four triangles (T1 to T4).

Figure 7C:
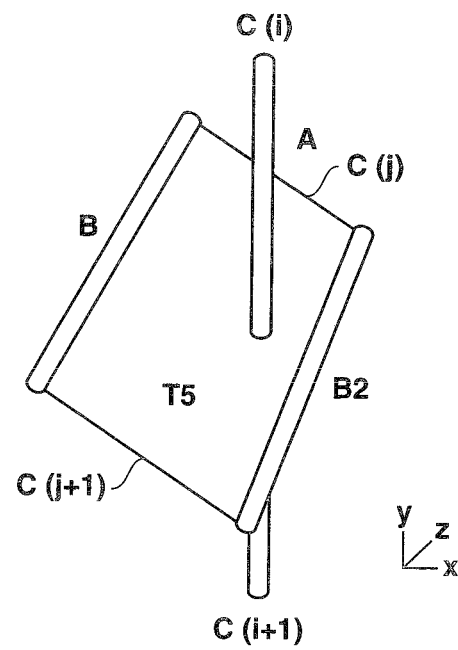

As shown in FIG. 7C, the determination portion 45 can also determine whether a "slipping through" phenomenon occurs by checking a relationship between the first straight line A and a quadrangle connecting four points of the both ends of the second straight line B and the both ends of the third straight line B2. But, a quadrangle connecting four points in a three-dimensional space is not in a two-dimensional plane and is a distorted quadrangle. Therefore, a further process is necessary to represents the quadrangle by a polygon. On the other hand, triangles having any three points among four points in a three-dimensional space as vertexes are all two-dimensional figures. Therefore, determination of passing through with a polygon using triangles is easy, and an error is less likely to occur in determination of whether a "slipping through" phenomenon occurs.
<Step S21>

The warning generating portion 46 generates a warning, based on information on occurrence of a "slipping through" phenomenon from the determination portion 45. The warning generated by the warning generating portion 46 may be a warning by publicly known sound, light, vibration, or the like, in addition to a visual warning displayed on the display portion 48 via the display image creating portion 47.

It is difficult for the endoscope shape analysis apparatus 1 to accurately identify an intersection relationship when the magnitude of the shortest vector between the straight lines between the coils is sufficiently small. Therefore, the endoscope shape analysis apparatus 1 preferably stops the above processes until the magnitude of the shortest vector of the straight lines between the coils is sufficient. Also, it is preferred to stop the above processes when there is no possibility that a "slipping through" phenomenon occurs, due to an operator's operation stage. In other words, the operator can start and stop the above processes as required.

The endoscope shape analysis apparatus 1 in the present embodiment determines occurrence of a position display error, based on previous position information and current position information of the insertion portion 20. Therefore, the endoscope shape analysis apparatus 1 can reliably discover occurrence of an error in position display of the insertion portion 20.

Second Embodiment

Next, a method for determining whether there is an error in position display of an insertion portion 20, that is, whether a "slipping through" phenomenon occurs, by an endoscope shape analysis apparatus 1B (not shown) in a second embodiment will be described using FIG. 8 to FIG. 10B. The endoscope shape analysis apparatus 1B in the present embodiment is similar to the endoscope shape analysis apparatus 1 in the first embodiment, and therefore, like components are referred to by like numerals, and description of the components is omitted.

Figure 8:
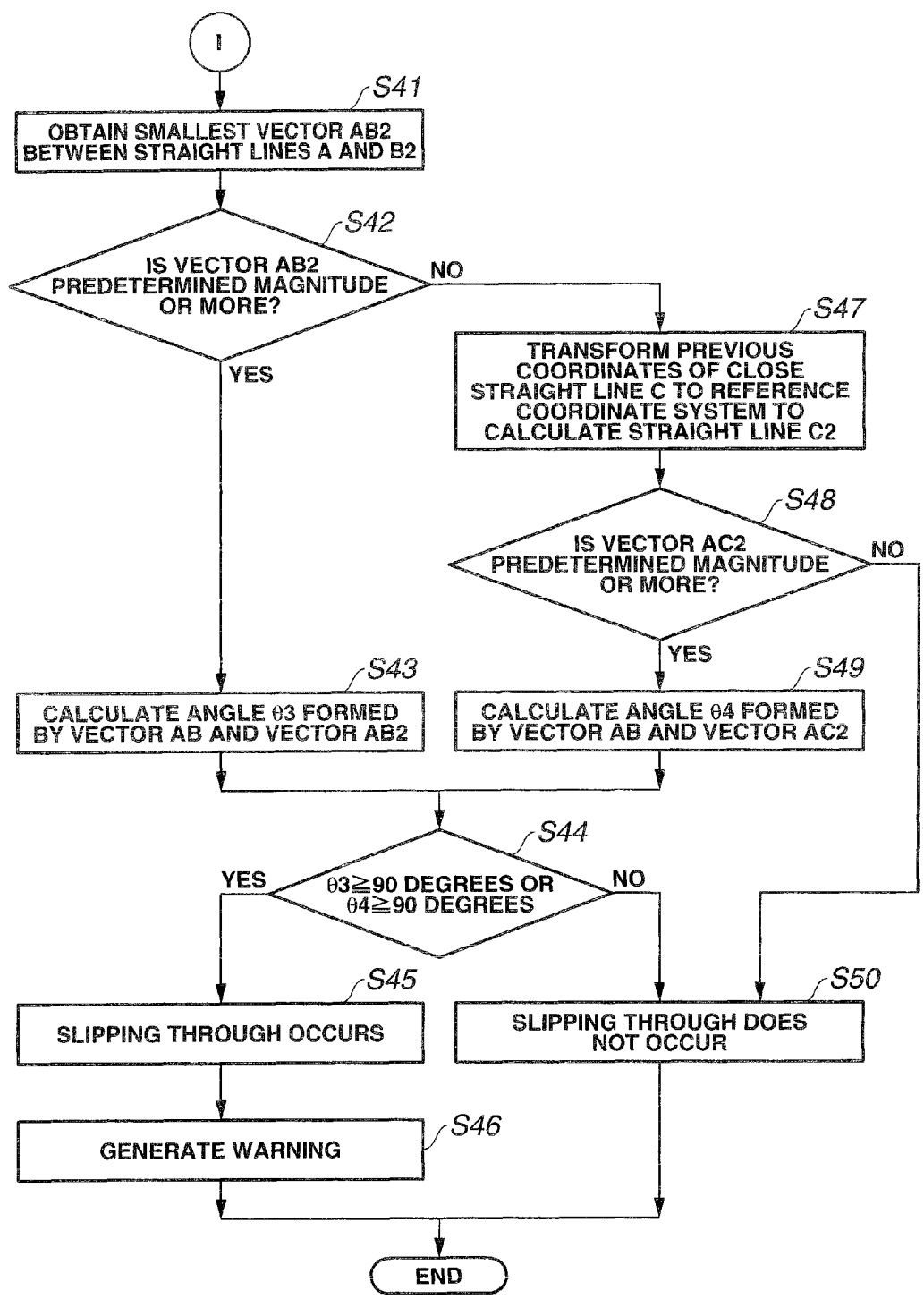
FIG. 8 is a flow chart for explaining a flow of operation of an endoscope shape analysis apparatus in a second embodiment.

A method for determining whether there is an error in position display of the insertion portion 20, that is, whether a "slipping through" phenomenon occurs, by the endoscope shape analysis apparatus 1B will be described below according to the flow chart of FIG. 8.

A configuration and part of operation of the endoscope shape analysis apparatus 1B in the present embodiment are similar to those of the endoscope shape analysis apparatus 1 in the first embodiment, and therefore, only different points will be described. In other words, the operation of the endoscope shape analysis apparatus 1B in the present embodiment is similar to that of the endoscope shape analysis apparatus 1 from steps S11 to S17 shown in FIG. 4, but a method for determining a position display error by the determination portion 45B is different.
<step S41>

Figure 9A:
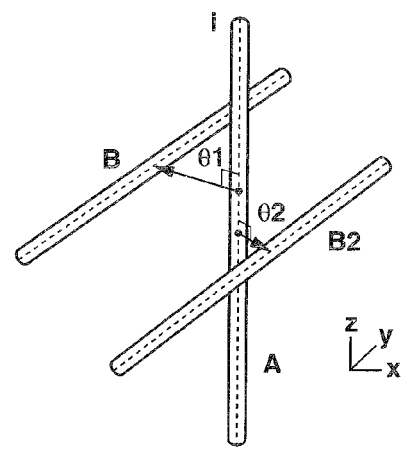
FIGS. 9A and 9B are explanatory diagrams for explaining operation of a determination portion in the second embodiment.

The determination portion 45B obtains a vector AB2 of smallest magnitude between a first straight line A and a third straight line B2, as shown in FIG. 9A. Here, the straight line A is orthogonal to a vector AB and the vector AB2, and θ1 and θ2 shown in FIG. 9A are both 90 degrees.

<Step S42>

The determination portion 45B determines whether the magnitude of the vector AB2 is a predetermined value or more. Here, the predetermined value is preferably K used in step S13, but a value different from K can also be used.

<Step S43>

Figure 9B:
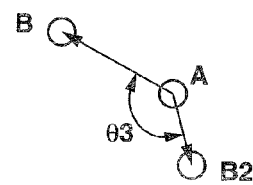

When the magnitude of the vector AB2 is the predetermined value or more (step S42: Yes), the determination portion 45B calculates an angle θ3 formed by the vector AB and the vector AB2. The vector AB of smallest magnitude between the first straight line A and a second straight line B has already been calculated in step S12. FIG. 9B shows the vector AB and the vector AB2 observed from a direction perpendicular to an axis of the straight line A.

<Steps S44 to S46>

The determination portion 45B determines that a "slipping through" phenomenon occurs when the angle θ3 formed by the vector AB and the vector AB2 is 90 degrees or more (Yes) (step S45), and a warning generating portion 46 generates a warning (step S46).

<Step S47>

Figure 10A:
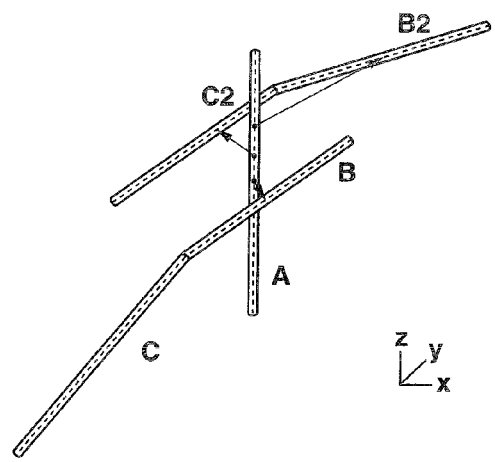
FIGS. 10A and 10B are explanatory diagrams for explaining operation of the determination portion in the second embodiment.

When the magnitude of the vector AB2 is less than the predetermined value (No) in step S42, the determination portion 45B transforms a straight line C adjacent to the straight line B from a previous straight line C1 to a reference coordinate system based on a current first straight line A by a method similar to that in step S17 to calculate a fourth straight line C2, as shown FIG. 10A.

This is performed in order that the determination portion 45B determines whether the insertion portion 20 moves largely, and a "slipping through" phenomenon occurs between the straight line B and the straight line C. The straight line C adjacent to the straight line B is a straight line adjacent to the straight line A, that is, a straight line having a vector of small magnitude, among two straight lines sharing any of source coils C(j) and C(j+1) at both ends of the straight line B.

<Step S48>

The determination portion 45B determines that there is no error in position display of the insertion portion 20 when a vector AC2 of smallest magnitude between the straight line A and the straight line C2 is less than a predetermined magnitude (step S50). Here, the predetermined value is preferably K used in step S14, but a value different from K can also be used.

<Step S49>

Figure 10B:
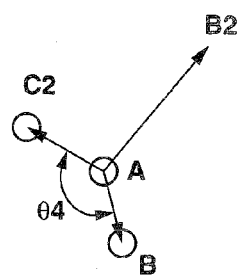

When the magnitude of the vector AC2 is the predetermined value or more (step S48: Yes), the determination portion 45B calculates an angle θ4 formed by the vector AB and the vector AC2. FIG. 10B shows the vector AB and the vector AC2 observed from a direction perpendicular to the axis of the straight line A.

<Step S44 to S46>

The determination portion 45B determines that a "slipping through" phenomenon occurs when the angle θ4 formed by the vector AB and the vector AC2 is 90 degrees or more (Yes) (step S45), and the warning generating portion 46 generates a warning (step S46).

<Step S50>

When the vector AC2 is less than the predetermined magnitude in step S48, and when the angle θ4 formed by the vector AB and the vector AC2 is less than 90 degrees in step S44, the determination portion 45B determines that a "slipping through" phenomenon does not occur, that is, there is no error in position display.

When the straight line C, which is one straight line among two straight lines adjacent to the first straight line A, has the vector AC2, which is a third vector shorter than the vector AB2, which is a second vector, and having a shortest length from the current first straight line A, after coordinate transformation with a transformation function regarding movement of the first straight line A, the determination portion 45B of the endoscope shape analysis apparatus 1B in the present embodiment determines whether there is an error in position display of the insertion portion 20, based on the angle θ4 formed by the vector AB, which is a first vector, and the vector AC2, which is the third vector.

The endoscope shape analysis apparatus 1B in the present embodiment determines occurrence of a position display error, based on previous position information and current position information of the insertion portion 20. Therefore, the endoscope shape analysis apparatus 1B can reliably discover occurrence of an error in position display of the insertion portion 20. Also, the endoscope shape analysis apparatus 1B determines occurrence of a position display error, based on vectors, and therefore, process is easy, in addition to effect of the endoscope shape analysis apparatus 1.

Third Embodiment

Next, a method for correcting a display image by an endoscope shape analysis apparatus 1C in a third embodiment of the present invention will be described using FIG. 11 to FIG. 20. The endoscope shape analysis apparatus 1C in the present embodiment is similar to the endoscope shape analysis apparatus 1 in the first embodiment, and therefore, like components are referred to by like numerals, and description of the components is omitted.

Figure 11:
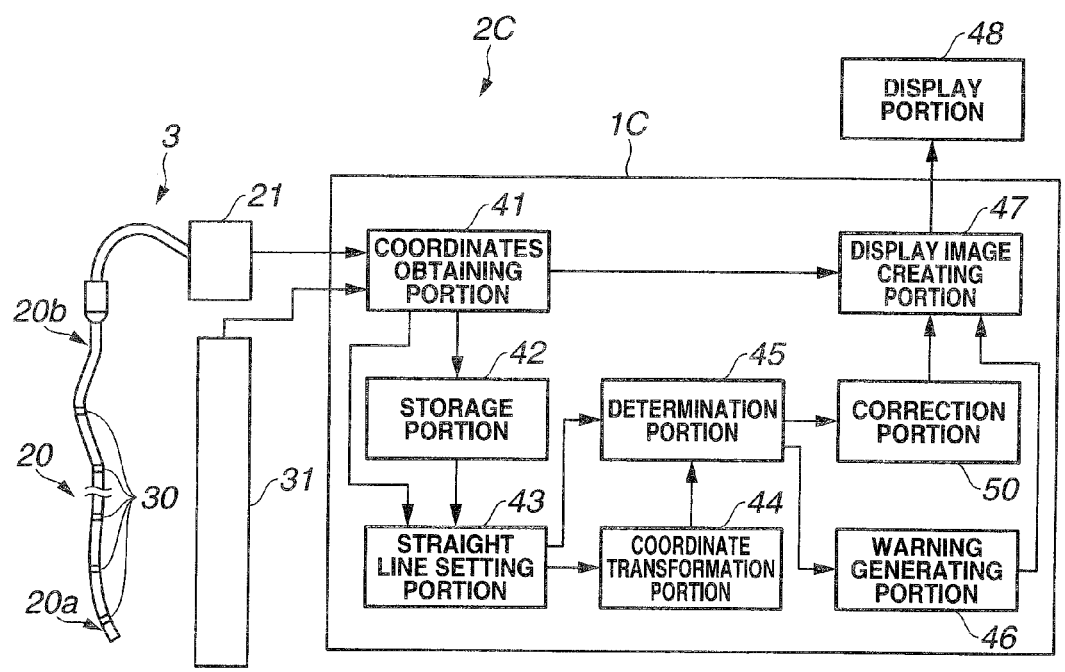
FIG. 11 is a configuration diagram for explaining a configuration of an endoscope shape analysis apparatus in a third embodiment.

As shown in FIG. 11, the endoscope shape analysis apparatus 1C of an endoscope system 2C in the present embodiment has a correction portion 50 for correcting a second straight line B, based on determination of a determination portion 45.

The method for correcting a display image by the endoscope shape analysis apparatus 1C will be described below according to the flow chart of FIG. 12. A configuration and part of operation of the endoscope shape analysis apparatus 1C in the present embodiment are similar to those of the endoscope shape analysis apparatus 1 in the first embodiment, and therefore, only different points will be described. In other words, the operation of the endoscope shape analysis apparatus 1C in the present embodiment from steps S61 to S70 is similar to the operation of the endoscope shape analysis apparatus 1 from second steps S11 to S20 shown FIG. 4, but steps S71 and S72 in which the second straight line B is corrected by the correction portion 50 is included.

<Step S69>

As in the endoscope shape analysis apparatus 1, the determination poriton 45 of the endoscope shape analysis apparatus 1C determines that a "slipping through" phenomenon occurs when a first straight line A passes through a plane of one or more of four triangles (T1 to T4).

A warning generating portion 46 may generate a warning, based on information on occurrence of a "slipping through" phenomenon from the determination portion 45, in order to notify the operator of the occurrence.

<Step S70 and Step S71>

The correction portion 50 performs correction of the straight line B by a correction method 1 when the determination portion 45 determines that an error in position display of an insertion portion 20 occurs. The correction method 1 is a correction method in which endpoints of the second straight line B are moved in a direction opposite to a direction of a shortest vector. An amount of movement of the endpoints of the straight line B by the correction method 1 is an amount obtained by adding a predetermined value to a magnitude F of a shortest vector AB. Here, for the predetermined value, the same value as the predetermined value K in step S63 can be used, but the predetermined value may be a different value. In other words, the straight line B is corrected to a straight line having a shortest vector of magnitude of the predetermined value from the straight line A.

<Step S72 and Step S73>

The correction portion 50 performs correction of the straight line B by a correction method 2 when the determination portion 45 determines that an error in position display of the insertion portion 20 does not occur. The correction method 2 is a correction method in which the endpoints of the second straight line B are moved in the direction of the shortest vector. An amount of movement of the endpoints of the straight line B by the correction method 2 is an amount obtained by subtracting the magnitude F of the shortest vector AB from a predetermined value. Here, for the predetermined value, the same value as the predetermined value in step S63 can be used, but the predetermined value may be a different value. In other words, the straight line B is corrected to a straight line having the shortest vector of magnitude of the predetermined value from the straight line A.

Figure 13A:
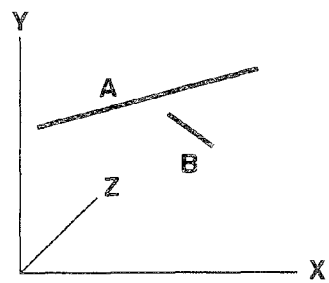
FIGS. 13A to 19 are explanatory diagrams for explaining operation of a correction portion in the third embodiment.
Figure 13B:
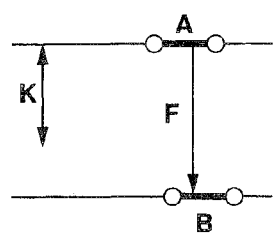
Figure 14A:
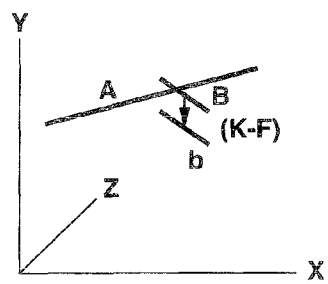
Figure 14B:
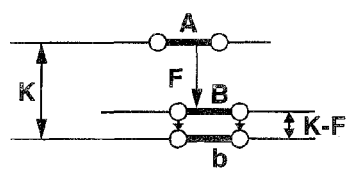
Figure 15A:
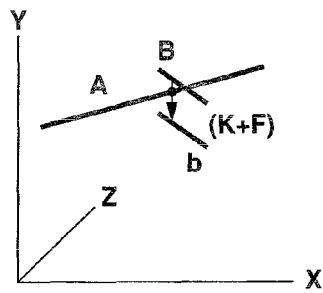
Figure 15B:
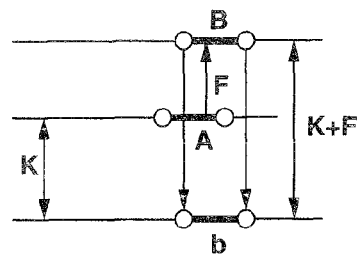

A correction method by the correction portion 50 will be described below using FIG. 13A to FIG. 15B. FIG. 13A and FIG. 13B are explanatory diagrams when the straight lines A and B are not close to each other. FIG. 14A and FIG. 14B are explanatory diagrams for explaining the correction method 2 when the straight lines A and B are close to each other, but a "slipping through" phenomenon does not occur. FIG. 15A and FIG. 15B are explanatory diagrams for explaining the correction method 1 when a "slipping through" phenomenon occurs.

FIG. 13A and FIG. 13B show a case where the magnitude F of the shortest vector AB between the straight lines A and B is the predetermined value K or more. FIG. 13A is a diagram showing the straight line A and the straight line B in a three-dimensional space. FIG. 13B is a diagram showing the straight line A and the straight line B in a plane including the shortest vector AB. A distance between the straight line A and the straight line B is large, and therefore, a discrimination difficulty phenomenon in an intersection portion is also less likely to occur. Therefore, the endoscope shape analysis apparatus 1 determines that there is no problem and does not perform subsequent processes.

FIG. 14A and FIG. 14B are explanation for explaining the correction method 2 when the magnitude F of the shortest vector AB between the straight lines A and B is less than the predetermined value K, but an error in position display does not occur. FIG. 14A is a diagram showing the straight line A, the straight line B, and a straight line b after correction in a three-dimensional space. FIG. 14B is a diagram showing the straight line A, the straight line B, and the straight line b after correction in a plane including the shortest vector AB. The straight line A and the straight line B are close to each other, and there is a possibility that a discrimination difficult phenomenon occurs. Therefore, the correction portion 50 performs correction in which the straight line B is moved away from the straight line A. Since the error in position display does not occur, correction is performed by the correction method 2, and the amount of movement of the endpoints of the straight line B is the amount obtained by subtracting the magnitude F of the shortest vector AB from the predetermined value, that is, (K−F).

FIG. 15A and FIG. 15B are explanation for explaining the correction method 1 when the magnitude F of the shortest vector AB between the straight lines A and B is less than the predetermined value K, and an error in position display occurs. FIG. 15A is a diagram showing the straight line A, the straight line B, and the straight line b after correction in a three-dimensional space. FIG. 15B is a diagram showing the straight line A, the straight line B, and the straight line b after correction in a plane including the shortest vector AB. The straight line A and the straight line B are close to each other, and there is a possibility that a discrimination difficult phenomenon occurs. Therefore, the correction portion 50 performs correction in which the straight line B is moved away from the straight line A. Since the error in position display occurs, correction is performed by the correction method 1, and the amount of movement of the endpoints of the straight line B is the amount obtained by adding the magnitude F of the shortest vector AB to the predetermined value, that is, (K+F).

Figure 16:
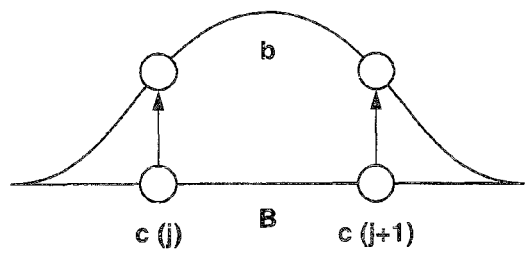
Figure 17:
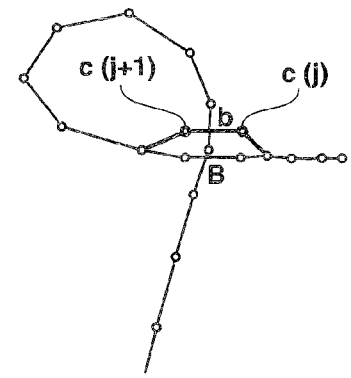

As a method for correcting the straight line B, preferably, coordinates of two source coils C(j) and C(j+1) at both ends of the straight line B are moved to the above-described predetermined coordinates, as shown in FIG. 16 and FIG. 17. Movement of the two source coils C(j) and C(j+1) means that not only the straight line B, but also two straight lines connected to the straight line B, that is, two straight lines sharing the source coils C(j) and C(j+1), are simultaneously moved.

Figure 18:
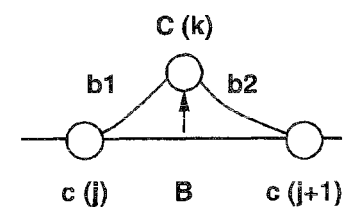
Figure 19:
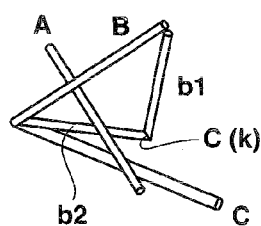

As a method for correcting the straight line B, a method can also be used in which a virtual source coil C (k) is inserted, that is, virtual coordinates are inserted, between the endpoints of the second straight line B, as shown in FIG. 18 and FIG. 19. In this case, the straight line B is corrected to be two straight lines b1 and b2. But, in a correction method in which one virtual source coil C (k) is provided as shown in FIG. 18, an unnatural shape is formed with a straight line C and the like connected to the straight line B, that is, correction may also cause failure. Therefore, when the virtual source coil C (k) is provided, two or more virtual source coils are preferably provided.

Also, when the correction portion 50 corrects the second straight line B, it is preferred to notify the operator that a displayed endoscope shape is a corrected shape. As the notification method, for example, a method in which a specific mark is displayed on a display screen of a display portion 48, a method in which the corrected straight line B is displayed with a special color, and the like can be used.

Figure 20:
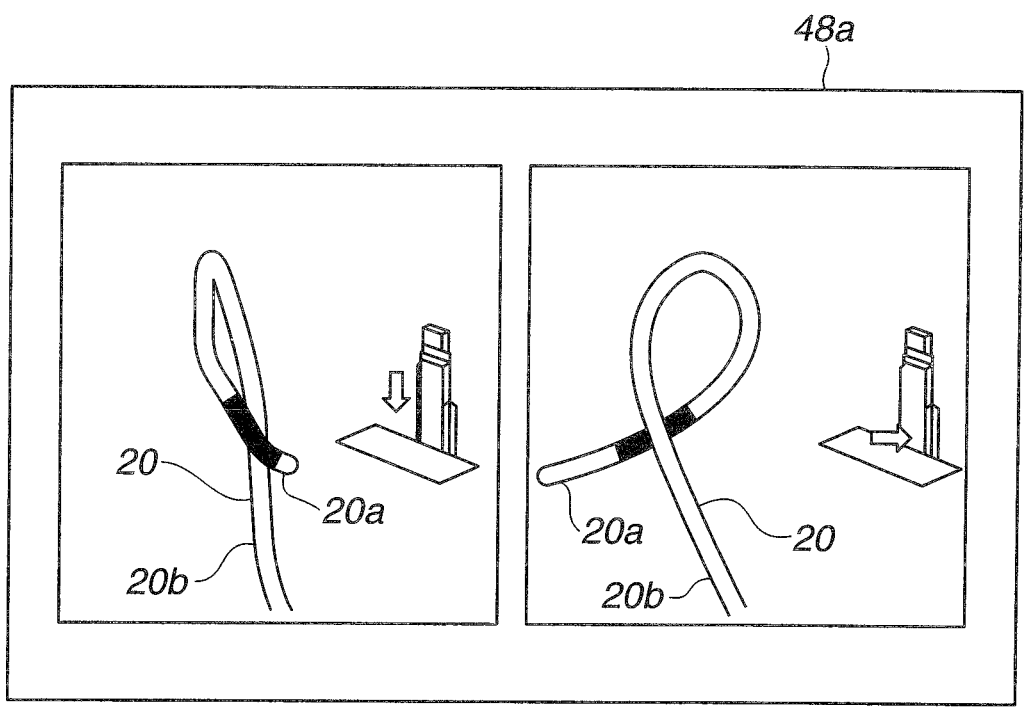
FIG. 20 is a diagram showing an example of display of a loop intersection portion of an insertion portion of the endoscope shape analysis apparatus in the third embodiment.

Further, the endoscope shape analysis apparatus 1 preferably has a display image creating portion 47 for differentiating at least any of display color or display brightness of the first straight line A and the second straight line B at least around endpoints of the shortest vector AB, as shown in FIG. 20, in order to enhance discrimination. FIG. 20 is a diagram showing one example of a display screen 48a of the display portion 48. The first straight line A and the second straight line B at least around the endpoints of the shortest vector AB are around an intersection portion of the insertion portion 20 on the display screen, and at least any of display color or display brightness of the entire first straight line A and second straight line B may be differentiated. The first straight line A and the second straight line B herein are for clearly showing four coordinate points used when the display image creating portion 47 forms an image of an insertion portion shape. An image actually displayed on the display screen is similar even if the image is a curve obtained by subjecting the first straight line A and the second straight line B to an interpolation process, as shown in FIG. 13, rather than the first straight line A and the second straight line B themselves.

The display image creating portion 47 performs the above process in which a form of display color and the like is made different for the first straight line A and the second straight line B set in a case of less than the predetermined value in the above step S13, but the display image creating portion 47 may perform a process according to a determination standard different from that in the above step S13.

By differentiating at least any of display color or display brightness of portions where the insertion portion 20 intersects, from each other, a front-back relationship of the insertion portion 20 in the intersection portions can be clearly discriminated by the operator.

The endoscope shape analysis apparatus 1C in the present embodiment corrects a shape of the insertion portion 20 to a shape with high discrimination, and therefore, discrimination of an endoscope shape is high, in addition to the effect of the endoscope shape analysis apparatus 1. The endoscope shape analysis apparatus 1C performs correction, particularly based on determination of whether there is an error in position display, and therefore, there is no correction error.

Modification 1 in Third Embodiment

As a modification of the endoscope shape analysis apparatus 1C in the above embodiment, an endoscope shape analysis apparatus using a method for determining whether there is an error in position display of an insertion portion 20, that is, whether a "slipping through" phenomenon occurs, by a different method will be described below.

In the present modification, first, the endoscope shape analysis apparatus calculates a shortest vector AB between a straight line A and a straight line B, and a shortest vector AB2 between the straight line A and a straight line B2 in order to determine whether there is an error in position display of the insertion portion 20. Further, the endoscope shape analysis apparatus 1 calculates an angle θ3 formed by the vector AB and the vector AB2. A determination portion 45 determines whether a "slipping through" phenomenon occurs, based on the angle θ3. The determination portion 45 determines that a "slipping through" phenomenon occurs when θ3 is 90 degrees or more. In other words, the determination portion 45 determines that there is an error in position display of the insertion portion 20 when the angle 83 formed by two vectors is 90 degrees or more.

In other words, the determination portion 45 of the endoscope shape analysis apparatus 1 in the present modification determines whether there is an error in position display of the insertion portion 20, based on the angle formed by the vector AB, which is a first vector having a shortest length from a current first straight line A to a current second straight line B, and the vector AB2, which is a second vector having a shortest length from the current first straight line A to a third straight line B2.

When a straight line C, which is one straight line among two straight lines adjacent to the first straight line A, has a vector AC2, which is a third vector shorter than the vector AB2, which is the second vector, and having a shortest length from the current first straight line A, after coordinate transformation with a transformation function regarding movement of the first straight line A, the determination portion 45 may determine whether there is an error in position display of the insertion portion 20, based on an angle θ4 formed by the vector AB, which is the first vector, and the vector AC2, which is the third vector.

The endoscope shape analysis apparatus in the present modification has effect similar to that of the endoscope shape analysis apparatus 1C in the third embodiment using determination of passing through with a polygon and further can perform processes at higher speed than that of the endoscope shape analysis apparatus 1C.

The present invention is not limited to the above-described embodiments and modification, and various changes and alterations can be made without departing from the spirit of the present invention.

What is claimed is:

1. An endoscope shape analysis apparatus comprising:
   a coordinates obtaining portion for obtaining a plurality of coordinate values of an insertion portion;
   a storage portion for storing the obtained plurality of coordinate values;
   a straight line setting portion for setting a first straight line and a second straight line, a position of which is compared with a position of the first straight line, based on the plurality of coordinate values;
   a coordinate transformation portion for transforming coordinates of a previous second straight line, based on a relative positional relationship between a previous first straight line stored in the storage portion and a current first straight line, to calculate a third straight line; and
   a determination portion for determining whether there is an error in a position display of the insertion portion from a positional relationship between the current first straight line, the current second straight line, and the third straight line.

2. The endoscope shape analysis apparatus according to claim 1, wherein the determination portion determines that there is the error in the position display of the insertion portion when the current first straight line passes through any one of four triangles having three points, among four points of both ends of the current second straight line and both ends of the third straight line, as vertexes.

3. The endoscope shape analysis apparatus according to claim 1, wherein the determination portion determines whether there is the error in the position display of the insertion portion, based on an angle formed by a first vector having a shortest length from the current first straight line to the current second straight line and a second vector having a shortest length from the current first straight line to the third straight line.

4. The endoscope shape analysis apparatus according to claim 3, wherein when one straight line adjacent to the first straight line has a third vector shorter than the second vector and having a shortest length from the current first straight line, after the coordinate transformation, the determination portion determines whether there is the error in the position display of the insertion portion, based on an angle formed by the first vector and the third vector.

5. The endoscope shape analysis apparatus according to claim 3, wherein the determination portion determines that there is the error in the position display of the insertion portion when the angle formed by the first vector and the second vector is 90 degrees or more.

6. The endoscope shape analysis apparatus according to claim 1, wherein the insertion portion comprises a plurality of magnetic field generating coils, and the coordinates obtaining portion detects the coordinate values by the magnetic field generating coils.

7. The endoscope shape analysis apparatus according to claim 1, further comprising a warning generating portion for generating a warning, based on determination of occurrence of the display error of the insertion portion by the determination portion.

8. An endoscope shape analysis apparatus comprising:
   a coordinates obtaining portion for obtaining a plurality of coordinate values of an insertion portion;
   a storage portion for storing the obtained plurality of coordinate values;

a straight line setting portion for setting a first straight line and a second straight line having a shortest vector of smallest magnitude from the first straight line, based on the plurality of coordinate values;

a coordinate transformation portion for transforming coordinates of a previous second straight line, based on a relative positional relationship between a previous first straight line stored in the storage portion and a current first straight line, to calculate a third straight line;

a determination portion for determining whether there is an error in a position display of the insertion portion from a positional relationship between the current first straight line, the current second straight line, and the third straight line; and a correction portion for correcting the second straight line, based on determination of the determination portion.

9. The endoscope shape analysis apparatus according to claim 8, wherein the determination portion determines that there is the error in the position display of the insertion portion when the current first straight line passes through any one of triangles having any three points, among four points of both ends of the current second straight line and both ends of the third straight line, as vertexes.

10. The endoscope shape analysis apparatus according to claim 8, wherein the determination portion determines whether there is the error in the position display of the insertion portion, based on an angle formed by a first vector having a shortest length from the current first straight line to the current second straight line and a second vector having a shortest length from the current first straight line to the third straight line.

11. The endoscope shape analysis apparatus according to claim 10, wherein the determination portion determines that there is the error in the position display of the insertion portion when the angle formed by the first vector and the second vector is 90 degrees or more.

12. The endoscope shape analysis apparatus according to claim 8, wherein the correction portion moves endpoints of the second straight line in a direction of the shortest vector when the determination portion determines that the error in the position display of the insertion portion does not occur.

13. The endoscope shape analysis apparatus according to claim 8, wherein the correction portion moves endpoints of the second straight line in a direction opposite to a direction of the shortest vector when the determination portion determines that the error in the position display of the insertion portion occurs.

14. The endoscope shape analysis apparatus according to claim 8, wherein the correction portion inserts virtual coordinates between endpoints of the second straight line in a direction opposite to a direction of the shortest vector when the determination portion determines that the error in the position display of the insertion portion occurs.

15. The endoscope shape analysis apparatus according to claim 8, comprising a display image creating portion for differentiating at least any one of display color or display brightness of the first straight line and the second straight line at least around endpoints of the shortest vector.

16. The endoscope shape analysis apparatus according to claim 8, wherein the insertion portion comprises a plurality of magnetic field generating coils, and the coordinates obtaining portion detects the coordinate values by the magnetic field generating coils.

17. An endoscope shape analysis apparatus comprising:

a plurality of magnetic field generating coils disposed in an insertion portion;

a coordinates obtaining portion for obtaining coordinate values by a sensing coil unit containing a plurality of sensing coils for detecting magnetic fields from the plurality of magnetic field generating coils;

a storage portion for storing the obtained plurality of coordinate values in a time series manner;

a straight line setting portion for setting a first straight line and a second straight line having a shortest vector of smallest magnitude from the first straight line, based on the plurality of coordinate values;

a coordinate transformation portion for transforming coordinates of a previous second straight line, using a quaternion as a transformation function, based on a relative positional relationship between a previous first straight line stored in the storage portion and a current first straight line, to calculate a third straight line;

a determination portion for determining that there is an error in a position display of the insertion portion when the current first straight line passes through any one of four triangles having three points, among four points of both ends of the current second straight line and both ends of the third straight line, as vertexes, according to determination of passing through with a polygon; and a correction portion for performing correction to move the second straight line away from the first straight line, based on determination of the determination portion.

18. The endoscope shape analysis apparatus according to claim 17, wherein the error in the position display is a "slipping through" phenomenon.

19. The endoscope shape analysis apparatus according to claim 18, comprising a display image creating portion for differentiating at least any one of display color or display brightness of the first straight line and the second straight line around an intersection portion.

\* \* \* \* \*